US007396856B2

(12) United States Patent
Hellberg et al.

(10) Patent No.: US 7,396,856 B2
(45) Date of Patent: Jul. 8, 2008

(54) BENZOPYRAN ANALOGS AND THEIR USE FOR THE TREATMENT OF GLAUCOMA

(75) Inventors: Mark R. Hellberg, Arlington, TX (US); Abdelmoula Namil, Arlington, TX (US)

(73) Assignee: Alcon, Inc., Hunenberg (CH)

(*) Notice: Subject to any disclaimer, the term of this patent is extended or adjusted under 35 U.S.C. 154(b) by 445 days.

(21) Appl. No.: 11/123,492

(22) Filed: May 6, 2005

(65) Prior Publication Data
US 2005/0209314 A1 Sep. 22, 2005

Related U.S. Application Data

(63) Continuation of application No. PCT/US03/39751, filed on Dec. 12, 2003.

(60) Provisional application No. 60/433,468, filed on Dec. 13, 2002.

(51) Int. Cl.
A61K 31/353 (2006.01)
C07D 311/20 (2006.01)
(52) U.S. Cl. .................... 514/457; 549/400
(58) Field of Classification Search ............... 514/457; 549/400
See application file for complete search history.

(56) References Cited

U.S. PATENT DOCUMENTS

| 4,690,931 | A | 9/1987 | Wick et al. | 514/317 |
|---|---|---|---|---|
| 5,011,846 | A | 4/1991 | Gittos et al. | 514/294 |
| 5,151,444 | A | 9/1992 | Ueno et al. | 514/530 |
| 5,290,781 | A | 3/1994 | Espino et al. | 514/259 |
| 5,296,504 | A | 3/1994 | Stjernschantz et al. | 514/530 |
| 5,352,708 | A | 10/1994 | Woodward et al. | 514/729 |
| 5,422,368 | A | 6/1995 | Stjernschantz et al. | 514/530 |
| 5,494,928 | A | 2/1996 | Bös | 514/415 |
| 5,538,974 | A | 7/1996 | Ogawa et al. | 514/253 |
| 5,561,150 | A | 10/1996 | Wichmann | 514/406 |
| 5,571,833 | A | 11/1996 | Kruse et al. | 514/414 |
| 5,578,612 | A | 11/1996 | Macor et al. | 514/323 |
| 5,646,173 | A | 7/1997 | Bös et al. | 514/411 |
| 5,652,272 | A | 7/1997 | Ogawa et al. | 514/652 |
| 5,693,654 | A | 12/1997 | Birch | 514/323 |
| 5,874,477 | A | 2/1999 | McConnell et al. | 514/657 |
| 5,889,052 | A | 3/1999 | Klimko et al. | 514/530 |
| 5,902,815 | A | 5/1999 | Olney et al. | 514/285 |
| 6,107,324 | A | 8/2000 | Behan et al. | 514/406 |
| 6,660,870 | B1 | 12/2003 | Ruskinko et al. | 548/307.4 |
| 6,664,286 | B1 | 12/2003 | May et al. | 514/415 |
| 6,696,476 | B2 | 2/2004 | Chen et al. | 514/403 |
| 6,806,285 | B1 | 10/2004 | May et al. | 514/416 |
| 6,884,816 | B2 | 4/2005 | May et al. | 514/405 |
| 2003/0181503 | A1 | 9/2003 | May et al. | 514/406 |

FOREIGN PATENT DOCUMENTS

| EP | 0 771 563 B1 | 1/2003 |
|---|---|---|
| WO | WO 92/00338 | 1/1992 |
| WO | WO 94/03162 | 2/1994 |
| WO | WO 94/13275 | 6/1994 |
| WO | WO 97/35579 | 10/1997 |
| WO | WO 98/18458 | 5/1998 |
| WO | WO 98/31354 | 7/1998 |
| WO | WO 98/56768 | 12/1998 |
| WO | WO 99/59499 | 11/1999 |
| WO | WO 00/12475 | 3/2000 |
| WO | WO 00/12510 | 3/2000 |
| WO | WO 00/16761 | 3/2000 |
| WO | WO 00/35922 | 6/2000 |
| WO | WO 00/44753 | 8/2000 |
| WO | WO 00/77002 | 12/2000 |
| WO | WO 00/77010 | 12/2000 |
| WO | WO 01/40183 | 6/2001 |
| WO | WO 01/70207 | 9/2001 |
| WO | WO 01/70222 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 01/85152 | 11/2001 |
| WO | WO 02/098350 | 12/2002 |
| WO | WO 02/098400 | 12/2002 |
| WO | WO 02/098860 | 12/2002 |
| WO | WO 03/051291 | 6/2003 |
| WO | WO 03/051352 | 6/2003 |
| WO | WO 03/053436 | 7/2003 |
| WO | WO 04/019874 | 3/2004 |
| WO | WO 04/028451 | 4/2004 |
| WO | WO 04/054572 | 7/2004 |
| WO | WO 04/058725 | 7/2004 |

OTHER PUBLICATIONS

King, Med. Chem: Principle and Practice (1994), p. 206-208.*
Bowen et al., "Nonlinear regression using spreadsheets," *Trends In Pharmacological Sciences*, vol. 16, pp. 413-423 (1995).
Chang et al., "Mechanism of the Ocular Hypotensive Action of Ketanserin," *J. of Ocular Pharmacology*, vol. 1(2), pp. 137-147 (1985).

(Continued)

Primary Examiner—Taofiq A Solola
(74) Attorney, Agent, or Firm—Kilyk & Bowersox, P.L.L.C.

(57) ABSTRACT

Novel benzopyran analogs are disclosed. Also disclosed are methods for the lowering and controlling of normal or elevated intraocular pressure as well as a method for the treatment of glaucoma using compositions containing one or more of the compounds of the present invention.

9 Claims, No Drawings

OTHER PUBLICATIONS

Gupta et al., "Therapeutic Potentials of 5-HT Receptor Modulators," *Indian J. of Pharmacology*, vol. 26, pp. 94-107 (1994).

Krootila et al., "Effect of Serotonin and Its Antagonist (Ketanserin) on Intraocular Pressure in the Rabbit," *J. of Ocular Pharmacology*, vol. 3(4), pp. 279-290 (1987).

Mallorga et al., "Characterization of Serotonin Receptors in the Iris + ciliary body of the albino rabbit," *Current Eye Research*, vol. 6(3), pp. 527-532 (1987).

Mano et al., "The Effect of Anplag (Sarpogelate HCL), New Selective 5-$HT_2$ Antagonist on Intraocular Pressure in Rabbits," *IOVS*, vol. 36(4), S719 (1995).

May et al., "A Novel and Selective 5-$HT_2$ Receptor Agonist with Ocular Hypotensive Activity: (S)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotensive Response of Serotonin 5-$HT_{1A}$ and 5-$HT_2$ Receptor Ligands in Conscious Ocular Hypertensive Cynomolgus Monkeys," *J. of Pharmacology and Experimental Therapeutics*, vol. 306(1), pp. 301-309 (2003).

Osborne et al., "Do Beta-Adrenoceptors and Serotonin 5-$HT_1$A Receptors have Similar Functions in the control of Intraocular Pressure in the Rabbit?", *Ophthalmologica*, vol. 210, pp. 308-314 (1996).

Osborne et al., "5-Hydroxytryptamine$_{1A}$ agonists: potential use in glaucoma. Evidence from animal studies," *Eye*, vol. 14(38), pp. 454-463 (2000).

Takeda et al., "The Effect of Inplag. Novel Selective 5-$HT_2$ Antagonist on Intraocular Pressure in Glaucoma Patients," IOVS, Vo. 36(4), S734 (1995).

Wang et al., "Effect of 5-methylurapldil, an $α_{1a}$- adrenergic antagonist and 5-hydroxytryptamine$_{1a}$ agonist, on aqueous humor dynamics in monkeys and rabbits," *Current Eye Research*, vol. 16(8), pp. 769-775 (1997).

Wang et al., "Effect of $_p$MPPI Hydrochloride (p-MPPI) Applied before 5-methylurapidill (5-MU) on Intraocular Pressure (IOP) In Normal Monkeys," *IOVS*, vol. 39(4) (1998).

\* cited by examiner

BENZOPYRAN ANALOGS AND THEIR USE FOR THE TREATMENT OF GLAUCOMA

This application is a continuation of PCT/US2003/039751, filed Dec. 12, 2003 and claims the benefit of priority from U.S. Provisional Patent Application No. 60/433,468, filed Dec. 13, 2002, which is incorporated in its entirety by reference herein.

BACKGROUND OF THE INVENTION

1. Field of the Invention

The present invention relates to various benzopyrans. These compounds are useful for lowering and controlling normal or elevated intraocular pressure (IOP) and for treating glaucoma.

2. Description of the Related Art

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308-314, 1996) teach that 8-hydroxydipropylantinotetralin (8-OH-DPAT) (a 5-$HT_{1A}$ agonist) reduces IOP in rabbits. Wang, et al. (Current Eye Research, Vol. 16(8):769-775, August 1997, and IVOS, Vol. 39(4), S488, March, 1998) indicate that 5-methylurapidil, an $\alpha_{1A}$ antagonist and 5-$HT_{1A}$ agonist lowers IOP in the monlkey, but due to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds are 5-$HT_{1B,D,E,F}$ agonists, e.g., sumatriptan and naratriptan and related compounds.

It has been found that serotonergic compounds which possess agonist activity at 5-$HT_2$ receptors effectively lower and control normal and elevated IOP and are useful for treating glaucoma, see commonly owned co-pending application, PCT/US99/19888, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 0077002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

U.S. Pat. No. 5,561,150 relates to substituted 2-(benzo[g] indazol-1-yl)-1-ethylamines and 2-(4H-indeno[1,2-c]pyrazol-1-yl)-1-ethylamine having preferential affinity for the 5-$HT_{2C}$ receptor as well as affinity for the 5-$HT_{2A}$ receptor. Further, it is mentioned that these compounds have utility for certain central nervous system disorders of therapeutic significance.

U.S. Pat. No. 5,646,173 relates to certain tricyclic pyrazole derivative compounds which are identified as being 5-$HT_{2C}$ agonists for the treatment of CNS diseases and are primarily directed to lipophilic analogs that have a high probability of entering the brain. Similarly, WO 98/56768 relates to tricyclic 5-$HT_{2C}$ agonists for the treatment of CNS diseases.

All of the patents, patent applications, and publications mentioned above and throughout are incorporated in their entirety by reference herein and form a part of the present application.

5-Hydroxytryptamine (serotonin) does not cross the blood-brain barrier and enter the brain. However, in order to increase brain serotonin levels the administration of 5-hydroxy-tryptophane can be employed. The transport of 5-hydroxy-tryptophane into the brain readily occurs, and once in the brain 5-hydroxy-tryptophane is rapidly decarboxylated to provide serotonin. Since the treatment of glaucoma is preferably with compounds that do not enter the CNS, relatively polar compounds that are 5-$HT_2$ agonists and have incorporated into their structure a phenolic hydroxyl group that can be considered comparable to that of serotonin, are of particular interest.

Accordingly, there is a need to provide compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are preferably 5-HT$_2$ agonists.

A feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling noirual or elevated intraocular pressure and/or treating glaucoma.

Another feature of the present invention is to provide compounds useful for binding and/or activating serotonin receptors in mammals, and especially in humans.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to methods to lower and/or control normal or elevated intraocular pressure by administering an effective amount of a composition containing a compound having Formula I as described below:

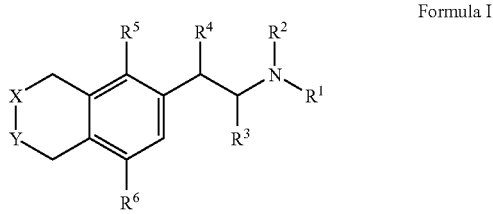

Formula I wherein $R^1$, $R^2$, $R^3$ are independently chosen from hydrogen or $C_{1-3}$alkyl;
$R^4$ is chosen from $R^1$ or $OR^1$;
$R^5$ is chosen from hydrogen, F, Cl, $OCONR^1R^2$, $OCOC_{1-3}$ alkyl, or $OR^7$;
$R^6$ is chosen from $OR^7$, $OCONR^1R^2$, $OCOC_{1-3}$ alkyl;
$R^7$ is chosen from hydrogen, $C_{2-4}$alkyl$CONR^1R^2$, $C_{2-4}$akyl$NR^1R^2$, $C_{2-4}$alkyl$CO_2H$, $C_{2-4}$alkyl$CO_2C_{2-4}$alkyl, $C_{1-3}$alkyl; wherein for $R^4$, $R^5$, $R^6$, and $R^7$, $R^1$ and $R^2$ are as defined above; and
X and Y are independently chosen from C or O, provided that if one of X or Y are O, the other is C;

and pharmaceutically acceptable salts and solvates of the compounds of Formula I.

In preferred aspects of the invention, at least one of $R^3$ or $R^1$ is an alkyl group such as $C_{1-3}$allyl, $R^5$ is hydrogen, F or $OR^7$ where $R^7$ is $C_{1-3}$alkyl. Preferably, at least one of $R^3$ or $R^4$ is a methyl group, and $R^5$ is $OR^7$ where $R^7$ is $C_{1-3}$alkyl. Most preferably, the compound is the R enantiomer, where $R^1$, $R^2$ are hydrogen, $R^3$ is a methyl group, and $R^5$ is $OR^7$ where $R^7$ is methyl.

The present invention also relates to a method for treating glaucoma, which involves administering an effective amount of a composition containing a compound having Formula I as described above.

The present invention further relates to the use of phanrmaceutical compositions containing at least one compound of Formula I.

In addition, the present invention relates to compounds represented by Formula I:

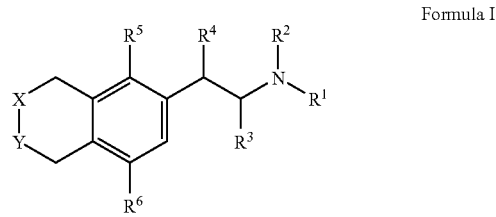

Formula I wherein $R^1$, $R^2$, $R^3$ are independently chosen from hydrogen or $C_{1-3}$alkyl;
$R^4$ is chosen from $R^1$ or $OR^1$;
$R^5$ is chosen from hydrogen, F, Cl, $OCONR^1R^2$, $OCOC_{1-3}$ alkyl, or $OR^7$;
$R^6$ is chosen from $OR^7$, $OCONR^1R^2$, $OCOC_{1-3}$alkyl;
$R^7$ is chosen from hydrogen, $C_{2-4}$alkyl$CONR^1R^2$, $C_{2-4}$akyl$NR^1R^2$, $C_{2-4}$alkyl$CO_2H$, $C_{2-4}$alkyl$CO_2C_{2-4}$alkyl, $C_{1-3}$alkyl; wherein for $R^4$, $R^5$, $R^6$ and $R^7$, $R^1$ and $R^2$ are as defined above; and
X and Y are independently chosen from C or O, provided that if one of X or Y are O, the other is C;

and pharmaceutically acceptable salts and solvates of the compounds of Formula I.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds that are useful according to the present invention. These compounds are generally represented by the following Formula I:

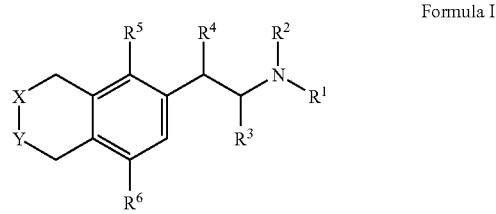

Formula I wherein $R^1$, $R^2$, $R^3$ are independently chosen from hydrogen or $C_{1-3}$alkyl;
$R^4$ is chosen from $R^1$ or $OR^1$;
$R^5$ is chosen from hydrogen, F, Cl, $OCONR^1R^2$, $OCOC_{1-3}$ alkyl, or $OR^7$;
$R^6$ is chosen from $OR^7$, $OCONR^1R^2$, $OCOC_{1-3}$alkyl;
$R^7$ is chosen from hydrogen, $C_{2-4}$alkyl$CONR^1R^2$, $C_{2-4}$alkyl$NR^1R^2$, $C_{2-4}$alkyl$CO_2H$, $C_{2-4}$alkyl$CO_2C_{2-4}$alkyl, $C_{1-3}$alkyl; wherein for $R^4$,$R^5$, $R^6$ and $R^7$, $R^1$ and $R^2$ are as defined above; and
X and Y are independently chosen from C or O, provided that if one of X or Y are O, the other is C;

and pharmaceutically acceptable salts and solvates of the compounds of Formula I.

Preferred Compounds are:

(+/−) 2-(5,8-Dimethoxy-isochroman-7-yl)-1-methyl-ethylamine
(+) 2-(5,8-Dimethoxy-isochroman-7-yl)-1-methyl-ethylamine
(−) 2-(5,8-Dimethoxy-isochroman-7-yl)-1-methyl-ethylamine
2-(5,8-Dimethoxy-isochroman-7-yl)-2-hydroxy-1-methyl-ethylamine
2-(5,8-Dimethoxy-isochroman-7-yl)-2-methoxy-1-methyl-ethylamine
2-(8-Fluoro-5-methoxy-isochroman-7-yl)-1-methyl-ethylamine
2-(5,8-Dimethoxy-isochroman-7-yl)-1,2-dimethyl-ethylamine or pharmaceutically acceptable salts and solvates of the above preferred compounds.

Most Preferred Compounds are:

(+/−) 2-(5,8-Dimethoxy-isochroman-7-yl)-1-methyl-ethylamine
(+) 2-(5,8-Dimethoxy-isochroman-7-yl)-1-methyl-ethylamine
(−) 2-(5,8-Dimethoxy-isochroman-7-yl)-1-methyl-ethylamine or pharmaceutically acceptable salts and solvates of the above preferred compounds.

It is recognized that compounds of Formula I can contain one or more chiral centers. This invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

In the formulas described above, the alkyl group can be straight-chain, branched, or cyclic and the like. Halogen includes Cl, Br, F, or I. Alkoxy is understood as an alkyl group bonded through an oxygen atom.

The following Examples are given to illustrate the preparation of compounds that are the subject of this invention but should not be construed as implying any limitations to the claims. The proton magnetic resonance spectrum of each compound of the Examples was consistent with the assigned structure.

SYNTHESIS

Methods of synthesizing the compounds of Formula I are illustrated by the following Examples. In the Examples, the following standard abbreviations are used g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectroscopy.

EXAMPLE 1

Synthesis of 2-(5,8-Dimethoxy-isochroman-7-yl)-1-methyl-ethylamine hydrochloride (Compound A)

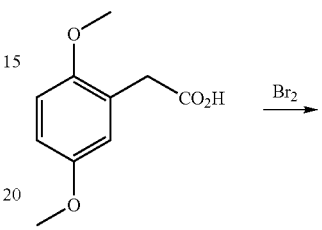

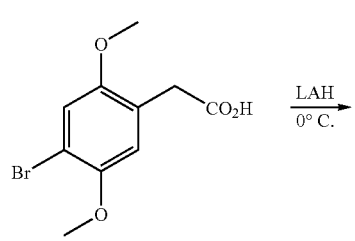

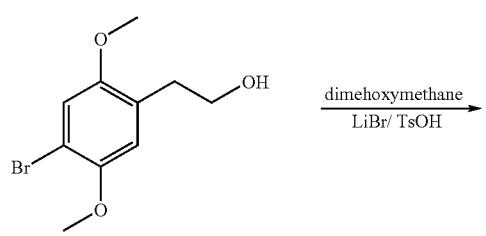

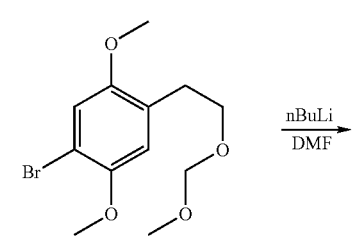

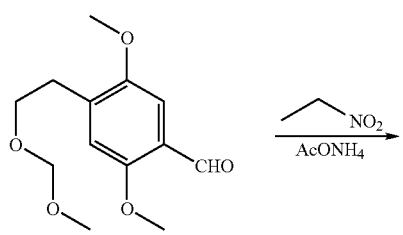

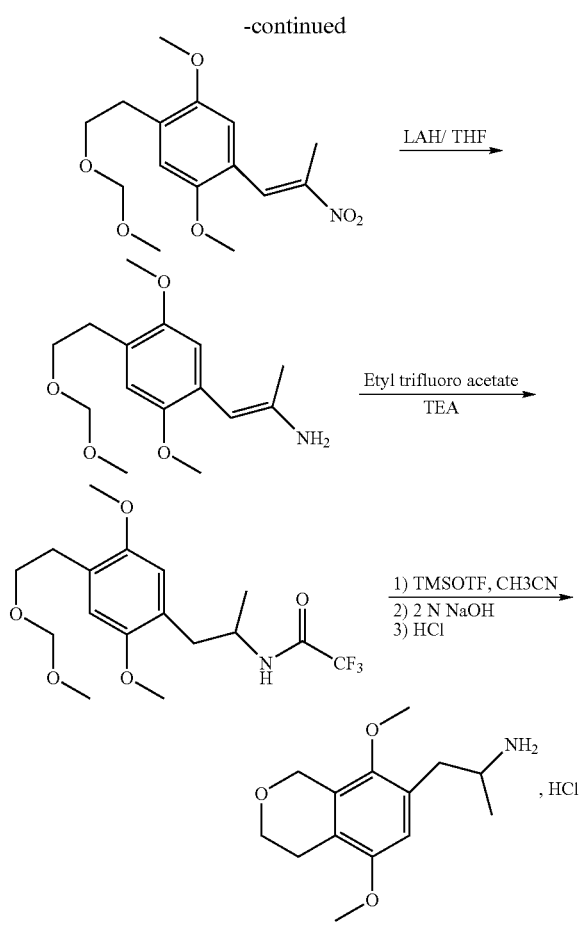

2-(5,8-Dimethoxy-isochroman-7-yl)-1-methyl-ethylamine hydrochloride

2-(4-Bromo-2,5-dimethoxy phenyl)-ethanol (2,5-Dimethoxy-phenyl)-acetic acid (3.00 g, 15.29 mmol) was dissolved in 30 ml of acetic acid and cooled to 0° C. To this solution was added bromine (2.44 g, 15.33 mmol), the reaction mixture was stirred overnight at room temperature and concentrated under reduced pressure, the solid residue was washed with cold hexane and dried overnight. The residue was dissolved in THF and cooled to 0° C. LAH (20 ml of 1.0 M in THF) was added slowly and then the reaction mixture was stirred at 0° C. for 2 h. Excess LAH was destroyed by careful addition of ethyl acetate and an aqueous solution of 0.10 M hydrogen chloride. The organic layer was separated, dried (MgSO$_4$) and concentrated under reduced pressure to give an oil (3.1 g), which solidifies slowly. MS (m/z) 278 (M+NH4)$^+$. $^1$HNMR(CDCl$_3$): δ ppm 2.86 (m, 2H), 378-3.84 (2s+m, 8H), 6.77 (s, 1H), 7.04 (s, 1H).

1-Bromo-2,5-dimethoxy-4-(2-methoxymethoxy-ethyl)-benzene

To a stirred solution of 2-(4-bromo-2,5-dimethoxy-phenyl)-ethanol (3.00 g, 11.49 mmol) in dimethoxymetlhane (30 ml) was added lithium bromide (1.00 g, 11.51 mmol) followed by p-toluenesulfonic acid monohydrate (0.10 g, 0.53 mmol). The reaction mixture was stirred at room temperature for 4 h and then partitioned between water and ethyl acetate (1/1). The organic layer was separated, dried (MgSO$_4$) and concentrated to give an oil, which was purified by flash chromatography using combi-flash column and a hexane and ethyl acetate gradient. MS (m/z) 322 (M+NH$_4$)$^+$. $^1$HNMR(CDCl$_3$): δ ppm 2.91 (m, 2H), 3.34 (s, 3H), 3.75 (m, 2H), 3.81 (s, 3H), 3.89 (s, 3H), 4.65 (s, 2H), 6.84 (s, 1H), 7.06 (s, 1H).

2,5-Dimethoxy-4-(2-methoxymethoxy-ethyl)-benzaldehyde

In a round bottom flask, 1-bromo-2,5-dimethoxy-4-(2-methoxymethoxy-ethyl)-benzene (0.55 g, 18.02 mmol) was dissolved in 30 mL of dry THF. The reaction mixture was cooled to −78° C. using a dry ice-acetone bath and stirred for 10 min. A solution of n-BuLi (0.86 mL of 2.5 M solution in hexane) was added and the reaction mixture was stirred for an additional 30 min. Dimethyl formamide (0.26 g, 36.06 mmol) was added and then the temperature was allowed warm up slowly to room temperature and stirred for 30 min. The reaction mixture was diluted with water and the organic material was extracted with ethyl acetate. The organic layer was dried (MgSO$_4$) and evaporated in vacuo. The crude material was purified by flash column chromatography using a hexane and ethyl acetate gradient to give colorless oil in 56% yield. MS (m/z) 255 (M+1)$^+$. $^1$HNMR(CDCl$_3$): δ ppm 2.96 (m, 2H), 3.32 (m, 3H), 3.75 (m, 2H), 3.79 (s, 3H), 4.13 (s, 3H), 4.63 (s, 2H), 6.98 (s, 1H), 7.26 (s, 1H), 10.40 (s, 1H).

1,4-Dimethoxy-2-(2-methoxymethoxy-ethyl)-5-(2-nitropropenyl)-benzene

A mixture of 2,5-dimethoxy-4-(2-methoxymethoxy-ethyl)-benzaldehyde (3.00 g, 11.80 mmol) and ammonium acetate (0.91 g 11.80 mmol) in nitroethane (10 mL) was stirred at 70° C. for 2 h. After allowing the reaction mixture to cool down to room temperature, the solvent was removed under vacuum. The oily residue was purified by flash chromatography using a hexane and ethyl acetate gradient to give 0.9 g of yellow oil. MS (m/z) 211. $^1$HNMR(CDCl$_3$): δ ppm 2.40 (s, 3H), 2.95 (m, 2H), 3.31 (s, 3H), 3.75 (m, 2H), 3.78 (s, 3H), 3.83 (s, 3H), 4.63 (s, 2H), 6.77 (s, 1H), 6.83 (s, 1H), 8.25 (s, 1H).

2-[2,5-Dimethoxy-4-(2-methoxymethoxy-ethyl)-phenyl]-1-methyl-ethylamine

To a cold solution (ice bath) of 1,4-Dimethoxy-2-(2-methoxymethoxy-ethyl)-5-(2-nitropropenyl)-benzene (0.83 g, 2.67 mmol) in 10 mL of dry THF was added dropwise a solution of 1 M LAH in THF (10.67 mL, 10.67 mmol). The reaction mixture was allowed to warm to room temperature and stir overnight. The excess lithium aluninLm hydride was decomposed by careful addition of 0.4 mL of water, 0.4 mL of 15% NaOH, and 1.2 mL of water. The reaction mixture was diluted with 50 mL of ethyl ether. The heterogeneous solution was stirred for 5 min and then filtered and the precipitate was washed with ethyl ether. The combined filtrates were dried (MgSO$_4$) and concentrated under reduced pressure to give a solid. MS (m/z) 284 (M+1)$^+$. $^1$HNMR(CDCl$_3$): δ ppm 1.03 (d, 3H), 2.46 (m, 1H), 2.65 (m, 2H), 2.83 (m, 2H), 3.25 (m, 3H), 3.65-3.75 (m, 9H), 4.56 (s, 2H), 6.59 (s, 1H), 6.66 (s, 1H).

N-{2-[2,5-Dimethoxy-4-(2-(methoxymethoxy-ethyl)-phenyl]-1-methyl-ethyl}-2,2,2-trifluoroacetamide Triethylainine (64 ul, 0.46 mmol) was added to a solution 2-[2,5-dimethoxy-4-(2-methoxymethoxy-ethyl)-phenyl]-1-methyl-ethylamine (0.1 g, 0.35 mmol) in methanol (5 mL). After 5 min, ethyl trifluoroacetate was added and the reaction mixture was stirred overnight at room temperature. The solvent was removed under vacuum. The residue was washed with hexane, and dried ($MgSO_4$) to give a white solid. MS (m/z) 397 (M+$NH_4^+$)$^+$. $^1$HNMR($CDCl_3$): δ ppm 1.25 (d, 3H), 2.80 (m, 2H), 2.90 (m, 2H), 3.29 (s, 3H), 3.65-3.75 (m, 8H), 4.10 ((m, 1H), 4.61 (s, 2H), 6.61(s, 1H), 6.77 (s, 1H), 7.26 (1H, NH).

2-(5,8-Dimethoxy-isochroman-7-yl)-1-methyl-ethylamine hydrochloride

To a solution of N-{2-[2,5-dimethoxy-4-(2-(methoxymethoxy-ethyl)-phenyl]-1-methyl-ethyl}-2,2,2-trifluoroacetamide (0.20 g, 5.27 mmol) in acetonitrile 5 mL, was added 2 drops of trimethylsilyl trifluoromethanesulfonate under nitrogen. The reaction mixture was heated at gentle reflux for 4 h and then cooled to room temperature. The volatiles were evaporated under reduced pressure to give N-[2-(5,8-dimethoxy-isochroman-7-yl)-1-methyl-ethyl]-2,2,2-trifluoroacetamide. This, was dissolved a 2 mL of methanol and cooled to 0° C. To this cold solution was added 2 mL of aqueous 2 N NaOH. The reaction mixture was allowed to warm to room temperature and stirred overnight. The reaction mixture was concentrated under reduced pressure and diluted with 10 ml of water. The organic material was extracted with dichloromethane (3×50 mL). The combined extracts were dried ($MgSO_4$), volatiles were removed under vacuum, and the residue was diluted in dry ethyl ether (40 mL). To this solution was added 1.0 M solution of hydrogen chloride in ethyl ether until no further precipitation. The solid formed (0.1 g) was collected by filtration. MS (m/z) 252 (M+1)$^+$. $^1$HNMR($D_2O$): δ ppm 1.28 (d, 3H), 2.71 (m, 2H), 2.95 (m, 2H), 3.65 (m, 1H), 3.71 (s, 3H), 3.98 (s, 3H), 4.00 (m, 2H), 4.82 (s, 2H), 6.81 (s, 1H). CHN analysis for $C_{14}H_{22}NO_3Cl+0.4H_2O+0.1\,CH_2Cl_2$). Calculated C55.80, H7.64, N4.60; Found C55.80, H7.38, N4.64

EXAMPLE 2

Synthesis of the (+) and (−) enantiomers of 2-(5,8-Dimethoxy-isochroman-7-yl)-1-methyl-ethylamine hydrochloride (Compounds B and C)

The (+) and (−) enantiomers of 2-(5,8-Dimethoxy-isochroman-7-yl)-1-methyl-ethylamine hydrochloride were prepared by HPLC separation of the racemate N-[2-(5,8-dimethoxy-isochroman-7-yl)-1-methyl-ethyl]-2,2,2-trifluoroacetamide prepared above using chiralpack, eluent (Hexane/EtOH (95/5)). These two enantiomers were 99% ee. The hydrolysis of the trifluoroacetamide groups and the transformation of the free amines to the corresponding hydrochloride salts were performed as outlined above.

(−) 2-(5,8-Dimethoxy-isochroman-7-yl)-1-methyl-ethylamine hydrochloride (Compound B)

MS (m/z) 251 (M+1)$^+$. $^1$HNMR (DMSO, $d_6$): δ ppm 1.13 (d, 3H), 2.50 (m, 2H), 2.51 (m, 1H), 2.56 (m, 1H), 3.50 (m, 1H), 3.61 (s, 3H), 3.82 (s, 3H), 3.84. (m, 2H), 4.66 (s, 2H), 6.71 (s, 1H), 8.08 (s, 3H, NH3+). $[α]_{405}$=−7.55, %C=0.649 in ethanol. CHN analysis for $C_{14}H_{22}NO_3Cl$. Calculated C58.43, H7.71, N4.87; Found C58.04, H7.73, N4.77

(+) 2-(5,8-Dimethoxy-isochroman-7-yl)-1-methyl-ethylamine hydrochloride (Compound C)

MS (m/z) 251(M+1)$^+$. $^1$HNMR (DMSO, $d_6$): $^1$HNMR (DMSO, $d_6$): δ ppm 1.13 (d, 3H), 2.56 (m, 2H), 2.69 (m, 1H), 2.93 (m, 1H), 3.50 (m, 1H), 3.61 (s, 3H), 3.82 (s, 3H), 3.84. (m, 2H), 4.66 (s, 2H), 6.81 (s, 1H), 8.08 (s, 3H, NH3+). $[α]_{405}$=+8.35, % C=0.503 in ethanol. CHN analysis for $C_{14}H_{22}NO_3Cl+0.2H_2O$). Calculated C57.71, H7.75, N4.81; Found C57.74, H7.63, N4.74

EXAMPLE 3

| Ingredients | Amount (wt %) |
| --- | --- |
| Compound A | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 4

| Ingredients | Amount (wt %) |
| --- | --- |
| Compound B | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 5

| Ingredients | Amount (wt %) |
| --- | --- |
| Compound C | 0.01-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 6

| Ingredients | Amount (wt %) |
| --- | --- |
| Compound A | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

The compounds of this invention, Formula I, can be incorporated into various types of ophthalmic formulations for delivery to the eye (e.g., topically, intracamerally, or via an iniplant). The compounds are preferably incorporated into topical ophthalmic fomnulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution fonmulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α1 antagonists (e.g., nipradolol), α2 agonists (e.g. iopidine and brimonidine), miotics (e.g., pilocarpine and epinepluine), prostaglandin analogs (e.g., latanoprost, travaprost, unoprostone, and compounds set forth in U.S. Pat. Nos. 5,889,052; 5,296,504; 5,422,368; and 5,151,444), "hypotensive lipids" (e.g., bimatoprost and compounds set forth in U.S. Pat. No. 5,352,708), and neuroprotectants (e.g., compounds from U.S. Pat. No. 4,690,931), particularly eliprodil and R-eliprodil, as set forth in a commoiy assigned WO 01/85152, and appropriate compounds from WO 94/13275, including memantine. All of the patents, applications, and publications are incorporated in their entirety by reference herein.

The compounds of the present invention preferably function as 5-$HT_2$ agonists and preferably do not enter the CNS. Compounds having the ability to be a 5-$HT_2$ agonist are beneficial for controlling IOP as well as the treatment of glaucoma as shown in International Published Patent Application No. WO 00/16761, incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm-blooded animals including humans. Preferably, an effective amount of the compound is administered to the patient such that the IOP is controlled or lowered to acceptable levels. Furthermore, the compounds of the present invention can be used to treat glaucoma in warm-blooded animals, including humans, by administering an effective amount of the compound to a patient in need of such treatment to treat the glaucoma.

METHOD 1

5-$HT_2$ Receptor Binding Assay

To determine the affinities of serotonergic compounds at the 5-$HT_2$ receptors, their ability to compete for the binding of the agonist radioligand [$^{125}$I]DOI to brain 5-$HT_2$ receptors is determined as described below with minor modification of the literature procedure [Neuropharmacology, 26, 1803 (1987)]. Aliquots of post mortem rat or human cerebral cortex homogenates (400 μL) dispersed in 50 mM Tris-HCl buffer (pH 7.4) are incubated with [$^{125}$I]DOI (80 μM final) in the absence or presence of methiothepin (10 μM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the $IC_{50}$ or $K_i$ value.

METHOD 2

5-$HT_2$ Functional Assay: $[Ca^{2+}]_i$ Mobilization

The receptor-mediated mobilization on intracellular calcium ($[Ca^{2+}]_i$) was studied using the Fluorescence Imaging Plate Reader (FLIPR) instrument. Rat vascular smooth muscle cells, A7r5, were grown in a normal media of DMEM/ 0% FBS and 10 μg/mL gentamycin. Confluent cell monolayers were trypsinized, pelleted, and re-suspended in normal media. Cells were seeded in a 50 μL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 mL) to each well of the 96-well plate and incubated with dye for 1 h at 23° C.

Typically, test compounds were stored at 25 µM in 50% DIVISO/50% Ethanol solvent. Compounds were diluted 1:50 in 90% DMSO/20% ethanol. For "hit" screening, compounds were further diluted 1:10 in FLIPR buffer and tested at a final concentration of 10 µM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000-12000 counts by modifying the exposure time, the camera F-stop, or the laser power. Instrument settings for a typical assay were the following: laser power 0.3-0.6 W, camera F-stop F/2, and exposure time 0.4 sec. An aliquot (25 µL) of the test compound was added to the existing 100 µL dye-loaded cells at a dispensing speed of 50 µL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response. When the compounds were tested as antagonists against 10 µM 5-HT, they were incubated with the cells for 15 minutes prior to the addition of 5-HT.

The above procedures were used to generate the data shown in Table 1.

TABLE 1

5-HT$_2$ Receptor Binding and Functional Data

| Compound | IC$_{50}$, nM | EC$_{50}$, nM | Efficacy (E$_{max}$, %) |
| --- | --- | --- | --- |
| Compound A | 2.99 | 267 | 55 |
| Compound B | 0.87 | 39 | 55 |
| Compound C | 1.34 | 43 | 69 |
| DOI | 0.33 | 30.2 | 31 |
| 5-HT | 0.941 | 80 | 107 |

METHOD 3

Acute IOP Response in Lasered (Hypertensive) Eyes of Conscious Cynomolgus Monkeys Intraocular pressure (IOP) can be determined with an Alcon Pneumatonometer after light corneal anesthesia with 0.1% proparacaine. Eyes are washed with saline after each measurement. After a baseline IOP measurement, test compound is instilled in one 30 µL aliquot to the right eyes only of nine cynomolgus monkeys. Vehicle is instilled in the right eyes of six additional animals. Subsequent IOP measurements are taken at 1, 3, and 6 hours.

Compound B, a 5-HT$_2$ agonist, significantly lowered IOP in the lasered monkey eye by 15.8% (6.8 mmHg), 28.5% (12.5 mmHg) and 21.3% (9.6 mmHg) at 1, 3, and 6 hours, respectively in lasered monkeys after a single topical ocular instillation of 300 µg Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A compound represented by Formula I:

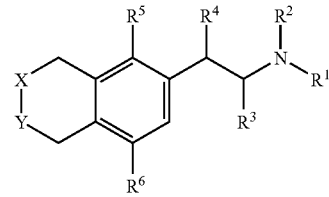

wherein $R^1$, $R^2$, $R^3$ are independently chosen from hydrogen or $C_{1-3}$alkyl;
$R^4$ is chosen from $R^1$ or $OR^1$;
R5 is chosen from hydrogen, F, Cl, $OCONR^1R^2$, $OCOC_{1-3}$alkyl, or $OR^7$;
$R^6$ is chosen from $OR^7$, $OCONR^1R^2$, $OCOC_{1-3}$alkyl;
$R^7$ is chosen from hydrogen, $C_{2-4}$alkylCONR$^1$R$^2$, $C_{2-4}$alkylNR$^1$R$^2$, $C_{2-4}$alkylCO$_2$H, $C_{2-4}$alkylCO$_2$C$_{2-4}$alkyl, $C_{1-3}$alkyl; wherein for $R^4$,$R^5$,$R^6$ and $R^7$, $R^1$ and $R^2$ are as defined above; and
X and Y are independently chosen from C or O, provided that if one of X or Y are O, the other is C;
or pharmaceutically acceptable salts of the compounds of Formula I.

2. The compound of claim 1, wherein said compound is selected from the group consisting of
(+/−) 2-(5,8-Dimethoxy-isochroman-7-yl)-1-methyl-ethylamine;
(+) 2-(5,8-Dimethoxy-isochroman-7-yl)-1-methyl-ethylamine;
(−) 2-(5,8-Dimethoxy-isochroman-7-yl)-1-methyl-ethylamine;
2-(5,8-Dimethoxy-isochroman-7-yl)-2-hydroxy-1-methyl-ethylamine;
2-(5,8-Dimethoxy-isochroman-7-yl)-2methoxy-1-methyl-ethylamine;
2-(8-Fluoro-5-methoxy-isochroman-7-yl)-1-methyl-ethylamine; and
2-(5,8-Dimethoxy-isochroman-7-yl)-1,2-dimethyl-ethylamine.

3. A pharmaceutical composition comprising the compound of claim 1 and at least one vehicle.

4. A method for the treatment of glaucoma comprising administering to a patient a pharmaceutically effective amount of a composition comprising at least one compound of Formula I:

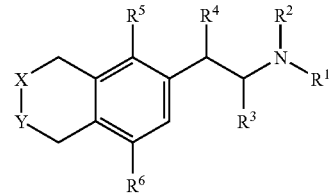

wherein $R^1$, $R^2$, $R^3$ are independently chosen from hydrogen or $C_{1-3}$alkyl;
$R^4$ is chosen from $R^1$ or $OR^1$;

$R^5$ is chosen from hydrogen, F, Cl, $OCONR^1R^2$, $OCOC_{1-3}$alkyl, or $OR^7$;

$R^6$ is chosen from $OR^7$, $OCONR^1R^2$, $OCOC_{1-3}$alkyl;

$R^7$ is chosen from hydrogen, $C_{2-4}$alkyl$CONR^1R^2$, $C_{2-4}$alkyl$NR^1R^2$, $C_{2-4}$alkyl$CO_2H$, $C_{2-4}$alkyl$CO_2C_{2-4}$alkyl, $C_{1-3}$alkyl; wherein for $R^4$, $R^5$, $R^6$ and $R^7$, $R^1$ and $R^2$ are as defined above; and X and Y are independently chosen from C or O, provided that if one of X or Y are O, the other is C;

or pharmaceutically acceptable salts thereof.

5. The method of claim 4, wherein $R^1$ and $R^2$ are hydrogens $R^3$ is $C_{1-3}$alkyl, $R^5$ is chosen from hydrogen, F or $OR^7$; and $R^7$ is $C_{1-3}$alkyl.

6. The method of claim 4, wherein said compound is selected from a group consisting of:

(+/−) 2-(5,8-Dimethoxy-isochroman-7-yl)-1-methyl-ethylamine (+) 2-(5,8-Dimethoxy-isochroman-7-yl)-1-methyl-ethylamine (−) 2-(5,8-Dimethoxy-isochroman-7-yl)-1-methyl-ethylamine 2-(5,8-Dimethoxy-isochroman-7-yl)-2-hydroxy-1-methyl-ethylamine 2-(5,8-Dimethoxy-isochroman-7-yl)-2-methoxy-1-methyl-ethylarnine 2-(8-Fluoro-5-methoxy-isochroman-7-yl)-1-methyl-ethylainine 2-(5,8-Dimethoxy-isochroman-7-yl)-1,2-dimethyl-ethylamine and pharmaceutically acceptable salts thereof.

7. A method of controlling normal or elevated intraocular pressure comprising administering to a patient a pharmaceutically effective amount of a composition comprising at least one compound of Formula I:

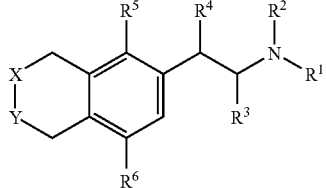

wherein $R^1$, $R^2$, $R^3$ are independently chosen from hydrogen or $C_{1-3}$alkyl;

$R^4$ is chosen from $R^1$ or $OR^1$;

$R^5$ is chosen from hydrogen, F, Cl, $OCONR^1R^2$, $OCOC_{1-3}$alkyl, or $OR^7$;

$R^6$ is chosen from $OR^7$, $OCONR^1R^2$, $OCOC_{1-3}$alkyl;

$R^7$ is chosen from hydrogen, $C_{2-4}$alkyl$CONR^1R^2$, $C_{2-4}$alkyl$NR^1R^2$, $C_{2-4}$alkyl$CO_2H$, $C_{2-4}$alkyl$CO_2C_{2-4}$alkyl, $C_{1-3}$alkyl; wherein for $R^4$, $R^5$, $R^6$ and $R^7$, $R^1$ and $R^2$ are as defined above; and X and Y are independently chosen from C or O, provided that if one of X or Y are O, the other is C;

or pharmaceutically acceptable salts thereof.

8. The method of claim 7, wherein $R^1$ and $R^2$ are hydrogens $R^3$ is $C_{1-3}$alkyl, $R^5$ is chosen from hydrogen, F or $OR^7$; and $R^7$ is $C_{1-3}$alkyl.

9. The method of claim 7, wherein said compound is selected from a group consisting of:

(+/−) 2-(5,8-Dimethoxy-isochroman-7-yl)-1-methyl-ethylamine;

(+) 2-(5,8-Dimethoxy-isochroman-7-yl)-1-methyl-ethylamine;

(−) 2-(5,8-Dimethoxy-isochroman-7-yl)-1-methyl-ethylamine;

2-(5,8-Dimethoxy-isochroman-7-yl)-2-hydroxy-1-methyl-ethylamine;

2-(5,8-Dimethoxy-isochroman-7-yl)-2-methoxy-1-methyl-ethylamine;

2-(8-Fluoro-5-methoxy-isochroman-7-yl)-1-methyl-ethylamine;

2-(5,8-Dimethoxy-isochroman-7-yl)-1,2-dimethyl-ethylamine;

and pharmaceutically acceptable salts thereof.

\* \* \* \* \*

UNITED STATES PATENT AND TRADEMARK OFFICE
CERTIFICATE OF CORRECTION

PATENT NO. : 7,396,856 B2  Page 1 of 1
APPLICATION NO. : 11/123492
DATED : July 8, 2008
INVENTOR(S) : Hellberg et al.

It is certified that error appears in the above-identified patent and that said Letters Patent is hereby corrected as shown below:

IN THE CLAIMS:

Column 14, Claim 1, line 20, "R5" should read --$R^5$--.

Column 15, Claim 6, line 27, "ethylarnine" should read --ethylamine--.

Column 15, Claim 6, lines 28-29, "ethy-lainine" should read --ethylamine--.

Signed and Sealed this

Twenty-sixth Day of August, 2008

JON W. DUDAS
*Director of the United States Patent and Trademark Office*